United States Patent [19]
Arnsten et al.

[11] Patent Number: 5,854,290
[45] Date of Patent: Dec. 29, 1998

[54] USE OF GUANFACINE IN THE TREATMENT OF BEHAVIORAL DISORDERS

[75] Inventors: Amy F. T. Arnsten, 376 Sperry Rd., Bethany, Conn. 06524; Patricia S. Goldman-Rakic, New Haven, Conn.; Robert H. Hunt, 1701 Cedar La., Nashville, Tenn. 37212

[73] Assignees: Amy F. T. Arnsten, Bethany; Patricia Goldman-Rakic, New Haven, both of Conn.; Robert H. Hunt, Nashville, Tenn.

[21] Appl. No.: 531,643

[22] Filed: Sep. 21, 1995

[51] Int. Cl.$^6$ .......................... A61K 31/65; A61K 31/155
[52] U.S. Cl. ............................. 514/617; 514/634
[58] Field of Search ...................... 514/634, 617

[56] References Cited

U.S. PATENT DOCUMENTS 4,847,300  7/1989  Arnsten et al. .......................... 514/617

OTHER PUBLICATIONS

Chappell et al, *Derwent Drug File Abstracts*, No. 95–27904, 1994.
Kunchandy et al, Chemical Abstracts, vol. 105, No. 23, abstract No. 203125d, 1986.
Hunt, Robert D. et al., Journal of The American Academy of Child Psychiatry, vol. 24, pp. 617–629 (1985).
Arnsten et al., "$\alpha_2$–Adrenergic Mechanisms in Prefrontal Cortex Associated with Cognitive Decline in Aged Nonhuman Primates", Science 230:1273–1276, 1985.
Arnsten et al., "Alpha–2 Adrenergic Agonists Decrease Distractibility in Aged Monkeys Performing the Delayed Response Task", Psychopharmacology 108:159–169, 1992.
Arnstein et al., "The Alpha–2 Adrenergic Agonist Guanfacine Improves Memory in Aged Monkeys Without Sedative or Hypotensive Side Effects: . . . ", The Journal of Neuroscience 8:4287–4298, 1988.
Arnsten et al., "Behavioral and Receptor Binding Analysis of The $\alpha_2$–Adrenergic Agonist, 5–Bromo–6 [2–Imidazoline–2–YL Amino] Quinoxaline (UK–14304): . . . ", Neuropharmacology 30:1279–1289, 1991.

Brown et al., "$\alpha_2$–Adrenoceptor Subtypes and Imidazoline–Like Binding Sites in The Rat Brain", British Journal of Pharamacology 99:803–809, 1990.
Chappel et al., "Guanfacine Treatment of Comorbid Attention–Deficit Hyperactivity Disorder and Tourette's Syndrome: Preliminary Clinical Experience", J. Am Acad Child & Adolescent Psychiatry 34:1140–1146, 1995.
Hunt et al., "An Open Trial of Guanfacine in the Treatment of Attention–Deficit Hyperactivity Disorder", J. Am. Acad Child Adolescent Psychiatry 34:50–56, 1995.
Sorkin et al., "Guanfacine A Review of its Pharmacodynamic and Pharmacokinetic Properties, and Therapeutic Efficacy in the Treatment of Hypertension", Drugs 31:301–336, 1986.
Steere et al., "The Alpha–2A Noradrenergic Agonist, Guanfacine, Improves Delayed Response Performance and Calms Behavior in Young Monkeys: . . . ", Soc. for Neurosci. Abstracts 20:831, 1994.3
Uhlen et al., "Delineation of Rat Kidney $\alpha_{2A}$– and $\alpha_{2B}$–adrenoceptors with [$^3$H]RX821002 Radioligand Binding: Computer Modelling . . . ", European Journal of Pharmacology 202:235–243, 1991.
Vigne et al., "Guanabenz, Guanochlor, Guanoxan and Idazoxan Bind with High Affinity to Non–adrenergic Sites in Pis Kidney Membranes", European Journal of Pharmacology 160:295–298, 1989.
Horrigan et al., "Guanfacine for Treatment of Attention–Deficit Hyperactivity Disorder in Boys", J. Child Adolesc. Psychopharm 5:215–223, 1995.
Kugler et al., "Differences in Psychic Performance with Guanfacine and Clonidine in Normotensive Subjects", Br. J. Clin. Pharmac., Supplement 1 10:71S–80S, 1980.

*Primary Examiner*—William R. A. Jarvis
*Attorney, Agent, or Firm*—Clark & Elbing LLP

[57] ABSTRACT

Disclosed is a method of treating disorders which have prominent symptoms of behavioral disinhibition (e.g., Attention-Deficit Hyperactivity Disorder, Conduct Disorder, Oppositional Defiant Disorder, Tourette's Syndrome, Lesch-Nyhan Syndrome, or the disinhibitory symptoms accompanying Post-traumatic Stress Disorder or dementia) in a primate with minimal sedative side effects by administering thereto a therapeutically effective amount of guanfacine.

12 Claims, 6 Drawing Sheets

USE OF GUANFACINE IN THE TREATMENT OF BEHAVIORAL DISORDERS

STATEMENT AS TO FEDERALLY SPONSORED RESEARCH

This invention was made with United States government support under contracts RO1 MH44866 from the National Institute of Health and Contract RO1 AG06036 from the National Institute of Aging.

BACKGROUND OF THE INVENTION

Attention-Deficit/Hyperactivity is a major disorder of childhood which often continues into the adult years. Patients with Attention-Deficit/Hyperactivity have difficulty concentrating and organizing their behavior. In addition, they are impulsive and easily distracted. Some display major hyperactivity while others outgrow or never show the motor symptoms. Attention-Deficit/Hyperactivity affects about 3.5 million children and adolescents in the United States, about half of whom retain attentional difficulties into adulthood (Cantwell and Baker, 1988). Attention-Deficit/Hyperactivity can result in low selfe-steem, poor relationships with peers and adults, and inferior performance in school. These difficulties can lead to serious emotional problems, truancy, drug abuse and criminal behavior (Pelham and Murphy, 1986). Moreover, the symptoms of Attention-Deficit/Hyperactivity commonly accompany those of Conduct Disorder (inappropriate aggression) and Tourette's Syndrome (inappropriate movements). Many of these same symptoms of disinhibited, inappropriate behaviors are also observed in elderly, demented individuals (e.g., agitation, wandering, inappropriate aggression). These disinhibited behaviors pose a serious problem to nursing homes and other caregivers.

This spectrum of disinhibited behaviors may arise from a dysfunction of the prefrontal cortex (A. F. T. Arnsten, J. C. Steere and R. Hunt, 1995). The prefrontal cortex projects to the brain's motor areas (striatum, motor cortices; Goldman-Rakic, P. S. et al., (1992) The Prefrontal Cortex and Internally Generated Motor Acts, Current Opinion Neurobiol. 2:830–835) and thus functions to guide behavior appropriately. In addition, the prefrontal cortex may perform this function for intellectual and affective behaviors. Degeneration of the prefrontal cortex may produce disinhibited behavior in elderly demented individuals, while altered development of these systems may lead to childhood disorders such as Attention-Deficit/Hyperactivity, Conduct Disorder, and Tourette's Syndrome.

Because recent research efforts have focused almost exclusively on developing treatments for the memory problems of dementia, there have been few new treatments for this spectrum of disorders. This focus has resulted in little research directed to the disorders of childhood. Attention-Deficit/Hyperactivity is usually treated with methylphenidate (Ritalin™ commercially available from Ciba Pharmaceutical), an amphetamine-like compound which is helpful for many patients (Hunt et al., 1991). However, methylphenidate has many deleterious side-effects including insomnia, appetite suppression, irritability, attentional "sticking", perseverative thoughts, increased aggression, and stunted growth (Hunt, R. D. (1988) Attention Deficit Disorder: Diagnosis, Assessment and Treatment. In Handbook of Clinical Assessment of Children and Adolescents—A Biopsychosocial Approach. C. Kestenbaum and D. Williams (eds.), pp. 519–561; McBurnett et al., 1991; Tannock and Schachar, 1992). Moreover, methylphenidate is contraindicated in patients with Conduct Disorder or Tourette's Syndrome because it can aggravate aggression and tics. Because many patients cannot tolerate methylphenidate, or find it only partially effective, alternative medications would be beneficial.

One alternative treatment for behavioral disorders has been the alpha-2 adrenergic agonist, clonidine (Hunt, R. D. et al., (1985) Clonidine Benefits Children with Attention Deficit Disorder and Hyperactivity: Report of a Double-Blind Placebo-Controlled Crossover Study, J. Amer. Acad. Child Psych., 24(5):617–629; 1986). Clonidine is particularly useful in Attention-Deficit/Hyperactivity patients who are very aggressive and/or highly aroused (Hunt, R. D. et al., (1990) Clonidine in Child and Adolescent Psychiatry, J. Child & Adol. Psychopharm., 1:87–101). However, it also has significant adverse side effects, including hypotension, "withdrawal" effects due to its short half life, and excessive sedation (ibid). It has been commonly assumed that the sedative action of clonidine is responsible for its beneficial effects in Attention-Deficit/Hyperactivity patients. It was presumed that clonidine attenuates noradrenergic tone, thereby decreasing arousal to near optimal levels (ibid). It was also presumed that clonidine improved Tourette's syndrome by a similar mechanism (Leckman, J. F. et al., (1989) Clonidine Treatment of Gilles de la Tourette Syndrome, Arch. Gen. Psychiatry, 48 324–328). Thus, even though the sedation itself often interfered with academic performance and other activities, the sedative side effects of clonidine treatment were thought to be essential for the beneficial effects of the drug.

Guanfacine, another alpha-2 adrenergic agonist, is less sedating than clonidine in monkeys (Arnsten, A. F. T. et al. (1988) The alpha-2 adrenergic agonist guanfacine improves memory in aged monkeys without sedative or hypotensive side effects: Evidence for alpha-2 receptor subtypes, J. Neurosci., 8: 4287–4298) and in humans (Kugler, J. et al., (1980) Differences in Psychic Performance with Guanfacine and Clonidine in Normotensive Subjects, Br. J. Clin. Pharmacol. 99:803–809). However, because clonidine was presumed to have its beneficial effects through its sedating actions, guanfacine was assumed to be less effective than clonidine in treating Attention-Deficit/Hyperactivity and related disorders. Very low doses of guanfacine (e.g. 0.00001–0.001 mg/kg) or moderate does of clonidine (about 0.01–0.05 mg/kg) improve working memory performance in aged monkeys without hypotensive or sedative side effects (Arnsten, A. F. T. et al., U.S. Pat. No. 4,847,300 which is incorporated herein by reference; Arnsten, A. F. T. et al., (1985) Alpha-2 adrenergic mechanisms in prefrontal cortex associated with cognitive decline in aged non-human primates, Science, 230:1273–1276; Arnsten, A. F. T. et al., (1988) The alpha-2 adrenergic agonist guanfacine improves memory in aged monkeys without sedative or hypotensive side effects: Evidence for alpha-2 receptor subtypes, J. Neurosci., 8:4287–4298). In addition, guanfacine enhanced working memory and attention regulation in aged monkeys (Arnsten, A. F. T. et al., (1992) Alpha-2 adrenergic agonists decrease distractibility in aged monkeys performing a delayed response task, Psychopharm. 108:159–169). The beneficial effects of guanfacine were particularly evident under conditions where distracting stimuli were present (ibid).

Because of the large patient population suffering from behavioral disinhibition and the deficiencies associated with existing therapies, a significant need exists for a method of treating behavioral disinhibition having a low incidence of adverse side-effects, especially sedation.

SUMMARY OF THE INVENTION

The present invention features the use of an alpha-2A agonist for the treatment of behavioral disinhibition. More particularly, the present invention relates to the improvement of behavioral inhibition in patients with Attention-Deficit Hyperactivity Disorder, Conduct Disorder, Oppositional Defiant Disorder, Tourette's Syndrome, Lesch-Nyhan Syndrome, or the disinhibitory symptoms accompanying Post-traumatic Stress Disorder or dementia following treatment with the alpha-2A agonist, guanfacine. The symptoms improved by guanfacine treatment include, but are not limited to: agitation, hyperactivity, distractibility, inattention, impulsivity, disorganization, uncontrolled aggression, self-mutilation, and uncontrolled movements.

The method of the invention provides a method for treating a behavioral disinhibition in a primate without inducing excessive sedation. Preferably, the method is used for the treatment of hyperactivity, agitation, impulsivity, aggression, inattention, distractibility, disorganization, uncontrolled movements, and self-mutilation. Preferably, the alpha-2A agonist is UK14304, guanabenz, or lofexidine. Most preferably, the alpha-2A agonist is guanfacine.

Other features and advantages of the invention will be apparent from the following description of the preferred embodiments thereof, and from the claims.

DESCRIPTION OF THE PREFERRED EMBODIMENTS

The present invention is based on our discovery that the administration of guanfacine calms behavior without concomitant sedation in juvenile, adult or elderly primates with symptoms of behavioral disinhibition including hyperactivity, agitation, impulsivity, aggression, inattention, distractibility, disorganization, uncontrolled movements, and/or self-mutilation.

Figure 1:
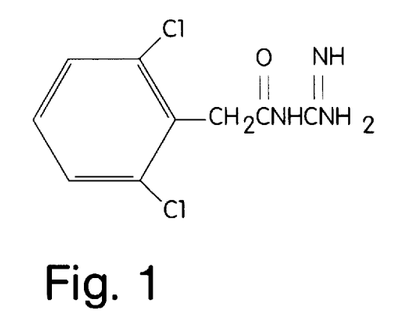
FIG. 1 is the chemical structure of guanfacine.

Referring to FIG. 1, the preferred active compound of the present invention is guanfacine (N-(Aminoiminomethyl)-2,6-dichlorobenzeneacetamide; N-amidino-2-(2,6 dichlorophenyl) acetamide). Guanfacine (Tenex™, commercially available from Wyeth Ayerst) is an α-2 noradrenergic agonist which has been available as an FDA approved hypotensive agent for over two decades. Guanfacine has several significant advantages compared to clonidine. Guanfacine has a longer excretion half-life (18 hours in adults; Sorken, E. M. et al., (1986) Guanfacine: A review of its pharmacodynamic and pharmacokinetic properties, and therapeutic efficacy in the treatment of hypertension, Drugs 31:301–336), and is less sedating and less hypotensive than clonidine (Kugler, J. et al., (1980) Differences in psychic performance with guanfacine and clonidine in normotensive subjects, Br. J. Clin. Pharmacol. 99:803–809). Guanfacine also has a more selective receptor binding profile than clonidine. Unlike clonidine, guanfacine does not bind significantly to α-1 receptors (Sorkin, E. M. et al., (1986) Guanfacine: A review of its pharmacodynamic and pharmacokinetic properties, and therapeutic efficacy in the treatment of hypertension, Drugs 31:301–336) or imidazoline receptors (Vigne, P. et al., (1989) Guanabenz, guanachlor, guanoxan, and idazoxan bind with high affinity to non-adrenergic sites in pig kidney membranes, Eur. J. Pharmacol., 160:295–298; Brown, C. M. et al., (1990) Alpha-2-adrenoceptor subtypes and imidazoline-like binding sites in the rat brain, Br. J. Pharmacol., 99:803–809). Guanfacine also displays a more selective profile within the family of α-2 receptors. Whereas clonidine binds equally well at the α-2A, α-2B, and α-2C subtypes, guanfacine exhibits selective binding for the α-2A site (Uhlen, S. et al., (1991) Delineation of rat kidney alpha 2A- and alpha 2B-adrenoceptors with [$^3$H] RX821002 radioligand binding: computer modelling reveals that guanfacine is an alpha 2A-selective compound, Eur. J. Pharmacol., 202:235–243).

We found that a low dose of guanfacine (0.001 mg/kg) was ineffective in a hyperactive, inattentive young monkey (see Table 1), but that higher doses of guanfacine do enhance prefrontal function and calm behavior without producing sedation. More particularly, higher doses of guanfacine improve behavior in hyperactive, inattentive, and impulsive young monkeys without the concomitant sedation associated with clonidine treatment. Guanfacine treatment similarly benefits human subjects with symptoms of behavioral disinhibition. Other compounds related to guanfacine that might be effective in the methods of the invention include all agonists with relative selectivity for the alpha-2A subtype of adrenergic receptor, such as UK14304 and guanabenz, or lofexidine.

EXAMPLES

General

The examples described herein report an evaluation of the effects of an alpha-2A adrengeric agonist, guanfacine, on cognitive performance and behavioral ratings in monkeys and on behavioral ratings in human patients.

Subjects

The animals used in the following examples were six peri-adolescent young monkeys (approximate ages of 2–5 years), 1 male and 5 female, and 4 female aged monkeys (approximate ages of 20–35 years). The monkeys were housed and cared for at Yale University School of Medicine, New Haven, Conn.

The human subjects consisted of children and adolescents with a range of behavioral disorders referred to one of the inventors, Dr. Hunt, for treatment at the Center for Attention and Related Disorders, Nashville, Tenn.

Subjects having Attention-Deficit/Hyperactivity Disorder included thirteen children and adolescents ranging in age from 4–20 (mean 11.1 years) (11 male and 2 female) with a DSM-IV diagnosis of Attention-Deficit/Hyperactivity Disorder. In addition, three subjects met criteria for Oppositional Defiant Disorder and one for learning disabilities. This group constitutes a population of middle class, motivated and cooperative subjects. Informed consent was obtained verbally and in writing after reviewing the potential benefits, side effects, and investigational nature of the use of guanfacine.

Guanfacine was also tested in six children and adolescents, ranging in age from 5 to 15 years, who met DSM-IV criteria for Tourette's syndrome.

Cognitive Testing (Monkey Studies)

In the following examples, the cognitive function of the prefrontal cortex was assessed using the Delayed Response Task Test. Results of this test are highly correlated with prefrontal cortical function in monkeys (P. S. Goldman-Rakic, 1987). Animals tested for highly palatable food rewards to optimize motivation. Five different delay lengths were used in the 30 trials which comprised a daily test session. Animals were tested twice weekly by an experimenter unaware of the drug testing conditions. All drug responses were compared to matched saline control responses. Relevant measures consisted of the number of completed and correct trials.

Rating Scales (Monkey Studies)

Two rating scales were utilized by the experimenter testing the monkey. One rating sale assessed the levels of sedation and the other assessed levels of aggression/docility. The ratings of sedation were as follows: 0=normal level of arousal; I=quiet or calm; II=sedated (drooping eyelids, slowed movements); III=intermittent sleeping; and IV=too sedated to finish testing. The ratings of agitation were as follows: –I=very alert; –II=slight agitation; –III=pronounced agitation; and –IV=too agitated to complete testing. Detailed descriptions of unusual behavior or behavioral changes were noted, including changes in aggressive or self-mutilatory behaviors.

Rating Scales (Clinical Studies)

Attention-Deficit/Hyperactivity symptoms were assessed using the Conners rating scales (Conners, C. K., (1973) Rating scales for use in drug studies with children, Amer. J. of Psych., 126:884–888) and related measures (Milich, R. et al., (1982) The independent dimensions of hyperactivity and aggression: A validation with playroom observation data, J. Abnormal Psych., 91:183–198). Follow-up measures using the same ratings were administered approximately one month after the initiation of guanfacine treatment.

Motor and phonic tics were assessed in patients with Tourette's Syndrome using a parent rated, 4 point tic rating scale as follows: 0 (no tics observed); 1 (mild tics observed; approximately less than one per hour); 2 (moderate tics observed; approximately one per five minutes); 3 (severe tics observed; approximately one or more per minute).

Drug Administration

Monkeys were injected intramuscularly with an acute dose of guanfacine (0.001–0.86 mg/kg), clonidine (0.02–0.05 mg/kg) or saline, 2 hours (guanfacine) or 15 min. (clonidine) prior to cognitive testing/behavioral assessment. There was generally at least a one week washout period between drug doses. Guanfacine and clonidine were dissolved in sterile saline under aseptic conditions.

Human subjects received chronic, oral guanfacine (Tenex™, 1 mg tablets) treatment.

Pharmacologic Treatment

In order to minimize side effects, guanfacine dosages were gradually increased from a low initial dosage of 0.5 mg/day to as much as 4 mg/day with a 0.5 mg increment every third day. Dosages were individually titrated for optimal clinical response. When patients were changing from other medications, the dosage of guanfacine was gradually increased while the previous medications were gradually decreased. The mean therapeutic dosage was 3.2 mg/day (0.091 mg/kg/day). Therapeutic administration at peak dose was generally divided into 0.5 mg in the morning, 0.5 mg at noon, 0.5 mg at approximately 4 pm, and 1.0 mg before bedtime.

Design and Analysis

Monkey data were analyzed using, within subjects, comparisons of performance on drug versus matched saline control. Delayed response performance was assessed using a paired t-test (t dep), while rating scale data utilized nonparametic statistics (Wilcoxon test). The p value for analyzing the monkey data was always p<0.05 for achieving significance.

To maintain the closest possible correlation with actual clinical practice, the initial investigation was conducted using a within subjects design. Dependent measures consisted of Conners' Attention-Deficit/Hyperactivity Disorder factor scores as well as changes in specific items on the Conners' Parent Questionnaire. Specific item differences were measured in anticipation of patterns of change resulting from guanfacine treatment that would not be identified by the specific item clusters defined by factor analysis. Therefore, the most specific patterns of change induced by this new treatment could be delineated. Statistical analysis utilized paired t-tests.

EXAMPLE 1

THE EFFECT OF ADMINISTERING CLONIDINE TO A YOUNG MONKEY

In Examples 1 and 2, drugs were administered to young monkeys with marked symptoms of hyperactivity, distractibility, inattention and aggressive behaviors due to longstanding personality traits or to the stress of recent entry into the colony. In addition, some of these animals exhibited self-mutilatory behaviors (e.g., self-biting). These symptoms disrupted normal cognitive testing. Example 1 involved prior art treatment with clonidine, while Example 2 employed guanfacine treatment of the invention.

Clonidine (0.02–0.05 mg/kg) or saline was administered to one young male (#636) and one young female (#643) rhesus monkey. Following saline administration, the monkeys were too agitated to test, completing an average of only 6 and 10 of the 30 trials attempted, respectively. Accuracy of response was also poor, averaging only 53.5% correct. Following 0.04 mg/kg clonidine, monkey #643 was too sedated to test. In contrast, 0.02 mg/kg clonidine improved performance markedly. This dose of clonidine was administered to this monkey on six separate occasions and each time the monkey completed all 30 trials. Accuracy of performance also improved to an average of 77% correct. Following saline administration, monkey #643 completed 10 of the 30 trials attempted, with only 40.0% chosen correctly. In contrast, following clonidine treatment (0.05 mg/kg), the monkey completed all 30 trials, performing 77% correct.

Figure 2A:
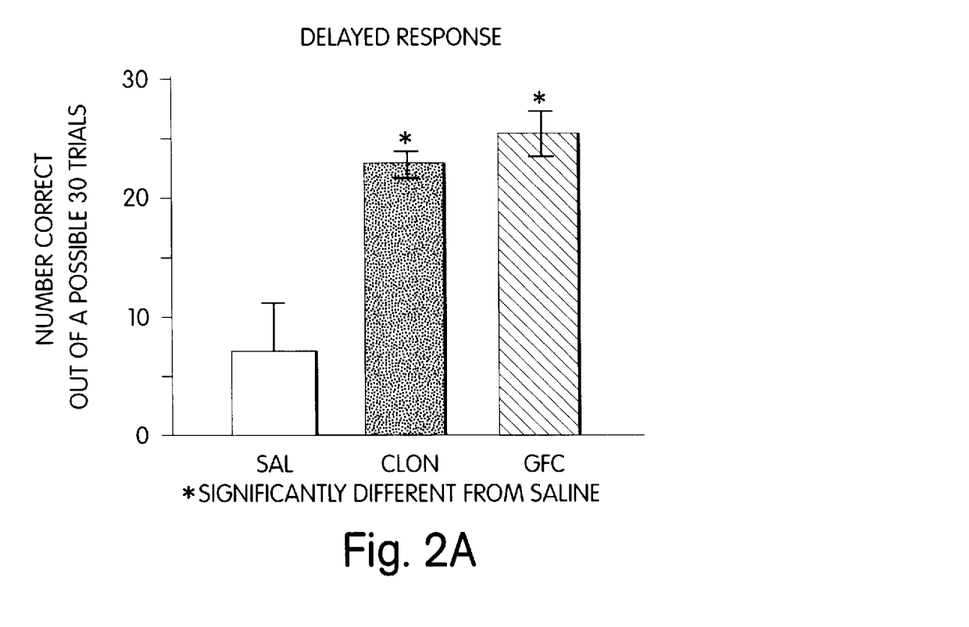
FIGS. 2A and 2B are graphs of young monkey data.
Figure 2B:
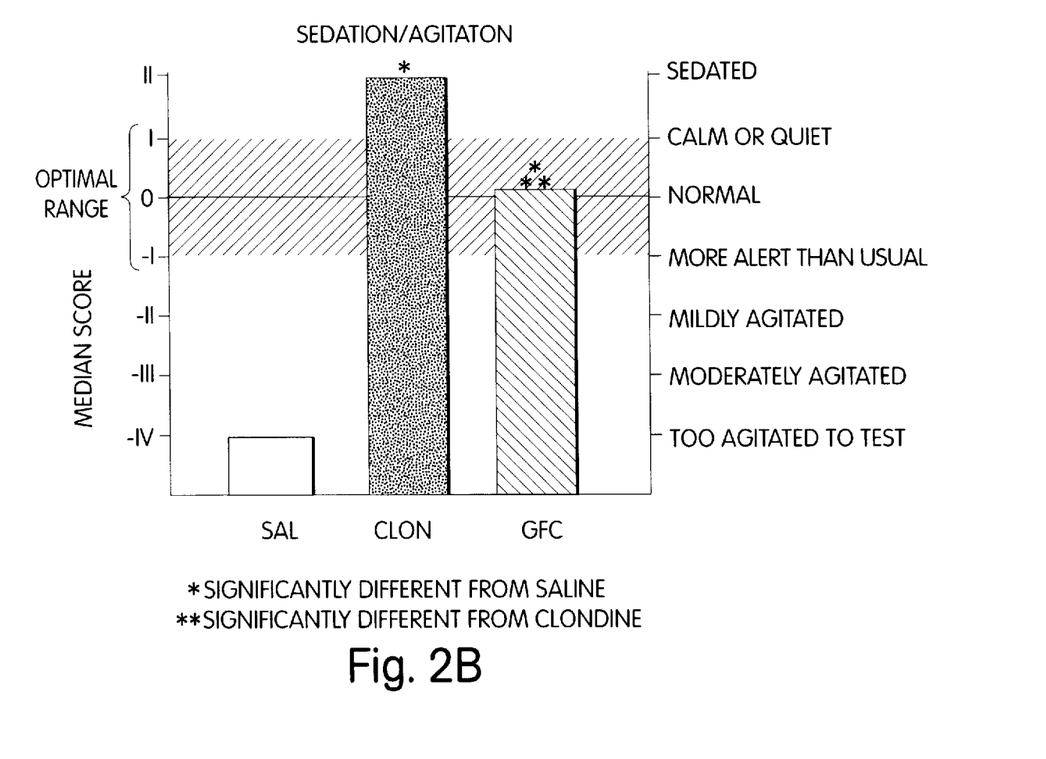
Figure 3A:
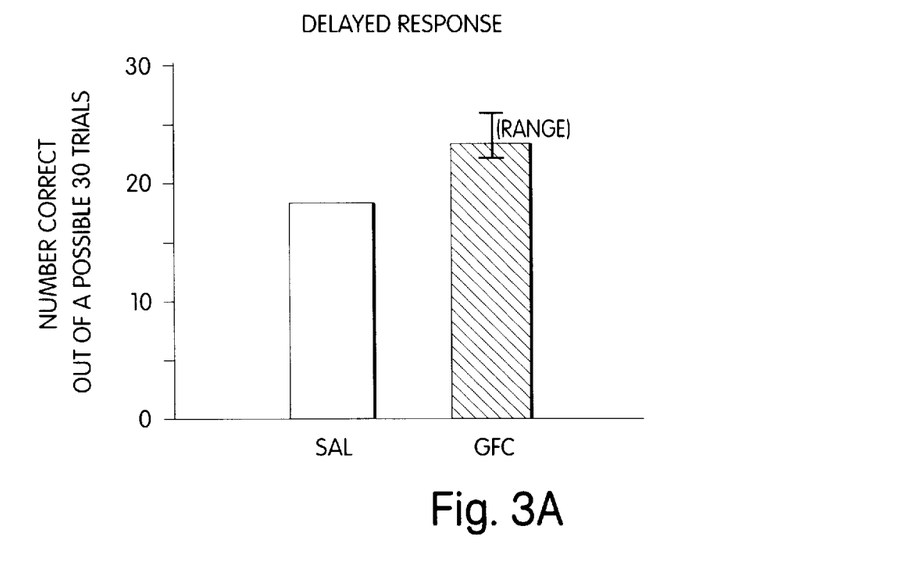
FIGS. 3A and 3B are graphs of aged monkey data.
Figure 3B:
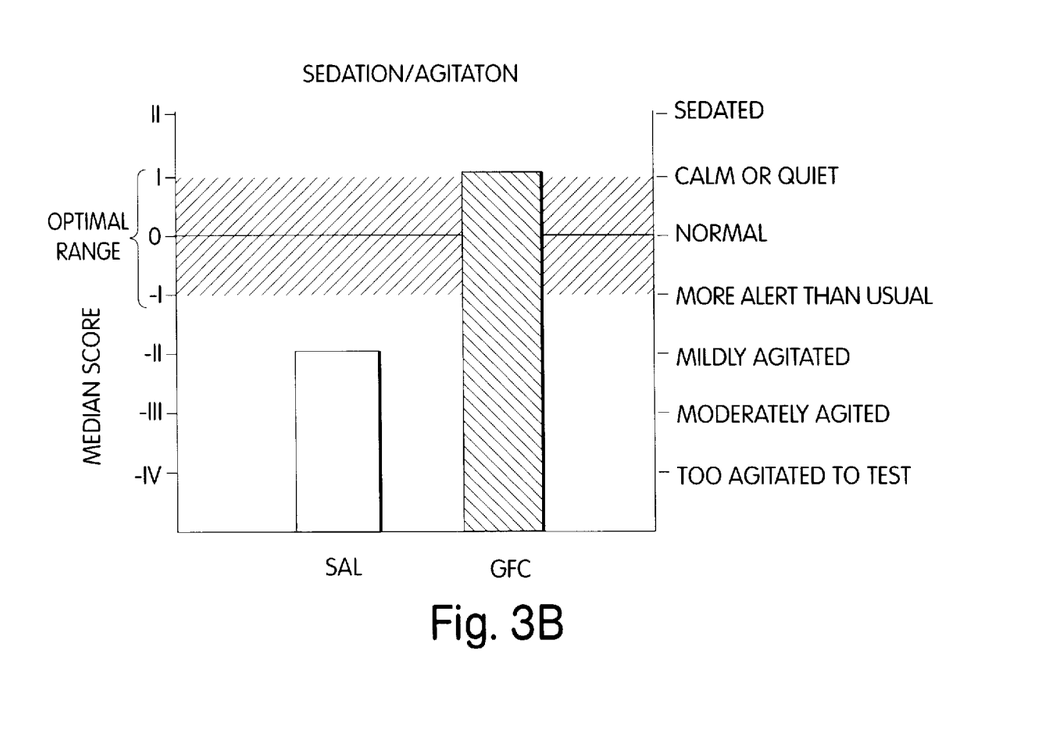

Marked sedation accompanied the improved performance of both animals. The median sedation score for both monkeys was a rating of II (i.e., sedated, drooping eyelids, slowed movements). A summary of these data can be seen in FIG. 2. This experimental profile is similar to the clinical effects of clonidine, where beneficial effects of clonidine are accompanied by significant sedation. This pattern of results suggested that the calming effects of clonidine result from its sedating actions.

EXAMPLE 2

THE EFFECT OF ADMINISTERING GUANFACINE TO YOUNG MONKEYS

Guanfacine was administered to the two young monkeys who had previously received clonidine. Although the lowest dose of guanfacine (0.001 mg/kg) did not improve the behavior of monkey #636, bhehavior became progressively better with increasing dose (see Table 1). Maximal improvement occurred with guanfacine doses ranging between 0.11–0.53 mg/kg range. Monkey #643 was tested repeatedly with 0.53 mg/kg guanfacine and was consistently improved (see Table 2). Importantly, neither animal exhibited symptoms of sedation following calming doses of guanfacine. A summary of the clonidine and guanfacine data can be seen in FIG. 2.

The calming effects of guanfacine were assessed in four additional adolescent female monkeys. The results of the monkey experiments are expressed as mean +/− S.E.M. These four monkeys completed an average of 11.1±2.1 of the 30 trials attempted and performed an average of 6.4±1.3 trials correctly following saline treatment. In contrast, the monkeys completed an average of 29.3±0.9 trials and performed an average of 23.1±1.8 correctly following 0.5 mg/kg guanfacine. Guanfacine also decreased agitation ratings without inducing sedation. Median agitation scores were −3.1±0.4 (i.e., agitation interfering with testing) and −0.4±0.7 (i.e., normal to more alert) following saline and guanfacine, respectively.

When the results from the six monkeys were combined for statistical analysis, guanfacine (0.5 mg/kg) improved significantly the number of trials completed (saline: 9.4±1.7; guanfacine: 29.5±0.6; t dep=9.41, df=5, p=0.0002) and the number of trials correct (saline: 5.6±0.9; guanfacine: 22.7±1.4; t dep=9.63, df=5, p=0.0002). This same dose of guanfacine significantly reduced agitation ratings without inducing sedation (saline: median score of −3.4±0.3; guanfacine: median score of −1.1±0.5; Wilcoxon p=−0.028). Guanfacine was also significantly less sedating than clonidine (Wilcoxon test on clonidine vs. guanfacine: p=0.004). Thus, guanfacine significantly calmed behavior without inducing sedation.

The experimenter's observations of the animals indicated that the monkeys exhibited fewer disinhibited behaviors following guanfacine treatment (see e.g. Tables 1 and 2). The monkeys engaged in less hyperactivity, circling, vocalization, aggression directed at the experimenter, self-mutilation (i.e., specifically a decrease in self-biting), and less inattentive or distracted behaviors. The animals appeared more focused, calm, and in control of their behavior.

EXAMPLE 3

THE EFFECT OF ADMINISTERING GUANFACINE VS. CLONIDINE TO AGED MONKEYS

The effects of administering guanfacine to aged monkeys with symptoms of behavioral disinhibition can be seen in Table 3. These highly-trained aged animals consistently completed all 30 trials of a test session. However, mild agitation interfered with accuracy of response in two monkeys (#447 and #124). Monkey #447 also exhibited aggressive behaviors following incorrect responses. Two additional animals (#446 and #448) who did not display agitation, but were very aggressive, provided the opportunity to observe the effects of guanfacine effects on aggression.

Similar to the effects in young monkeys, guanfacine (0.011–0.53 mg/kg) produced calming effects in aged monkeys. Agitation in monkeys #447 and #124 and aggression in monkeys #446, #447 and #448 were improved. These beneficial effects were observed without inducing sedation.

In contrast to guanfacine, the beneficial effects of clonidine were accompanied by sedative effects. Examples of the effects of clonidine can be seen in Table 4. Although these data were collected prior to the development of the agitation/sedation rating scales currently used, the experimenters' comments indicate that clonidine produced marked sedation.

EXAMPLE 4

THE EFFECT OF ADMINISTERING GUANFACINE TO CHILDREN AND ADOLESCENTS WITH ATTENTION-DEFICIT/ HYPERACTIVITY

Based on the calming effects of guanfacine in monkeys, the drug was tested in children and adolescents with Attention-Deficit Hyperactivity Disorder. Parents reported a significant improvement in their children's behavior and functioning during treatment with guanfacine as compared to without guanfacine. This result is supported by the reduction in the overall average score on Conners' Parents Questionnaire (t=2.55, p<0.015). The mean score before medication was 1.27 as compared to the mean score of 0.85 on guanfacine indicating that patients had significantly less Attention-Deficit/Hyperactivity Disorder symptoms during treatment.

Figure 4:
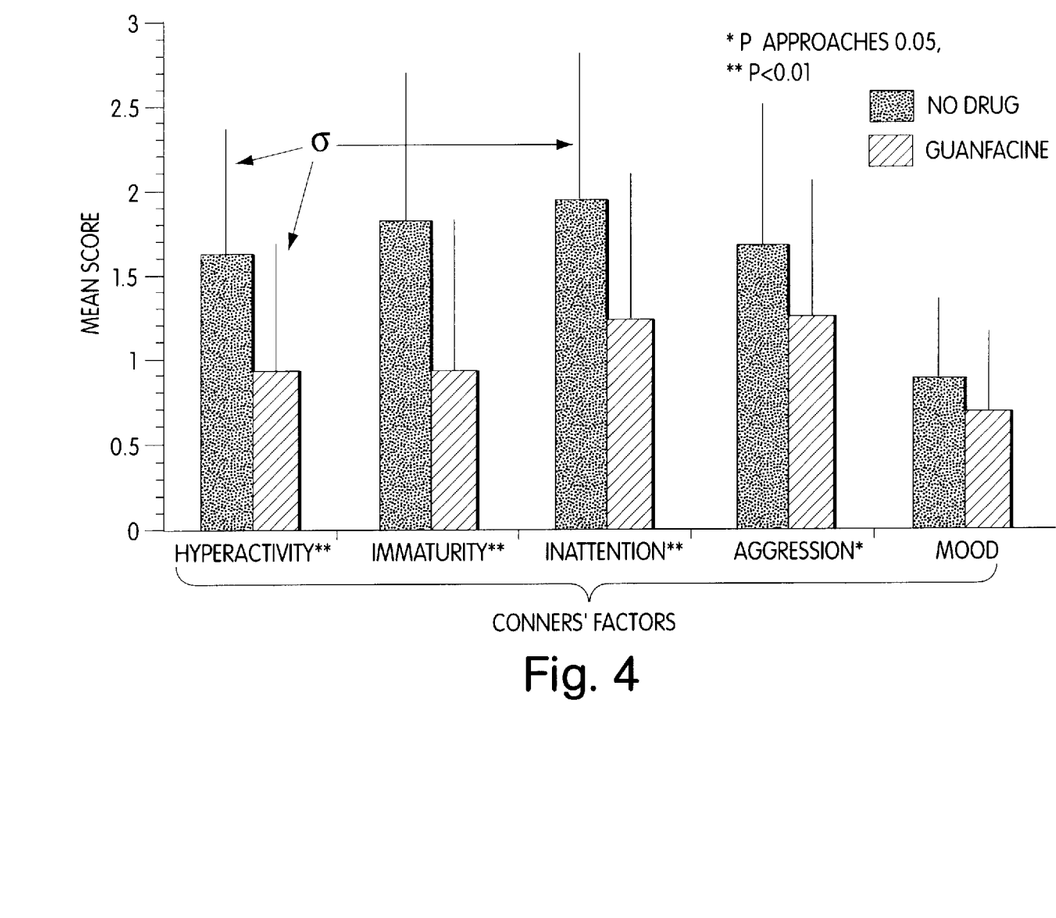
FIG. 4 is a graph depicting the effects of guanfacine in Attention-Deficit Hyperactivity Disorder subjects on Conners rating factors I–V.

Assessment of the Conners' Factors (see FIG. 4) showed a decrease in mean symptoms of hyperactivity (Factor 1: 1.63 off medication, 0.94 on guanfacine; t=3.69, p<0.002), inattention (Factor II: 1.92 off, 1.21 on, t=3.32, p<0.004), and immaturity (Factor V: 1.81 off, 0.92 on, t=3.77, p<0.002). No differences were observed in mood (Factor III) or aggression/opposition (Factor IV), although there was a trend for aggression to be improved. The three patients with symptoms of conduct disorder were rated as more cooperative and less quarrelsome with guanfacine treatment.

Figure 5A:
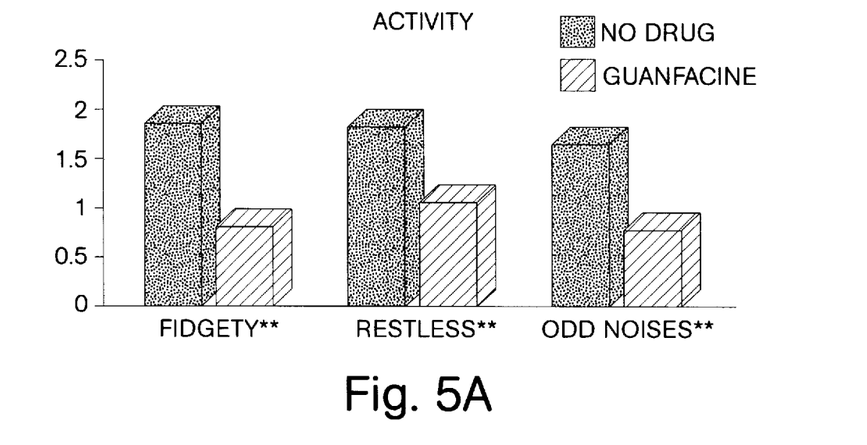
FIGS. 5A–5D are graphs depicting the effects of guanfacine in Attention-Deficit Hyperactivity Disorder subjects on Conners parent ratings of specific items.
Figure 5B:
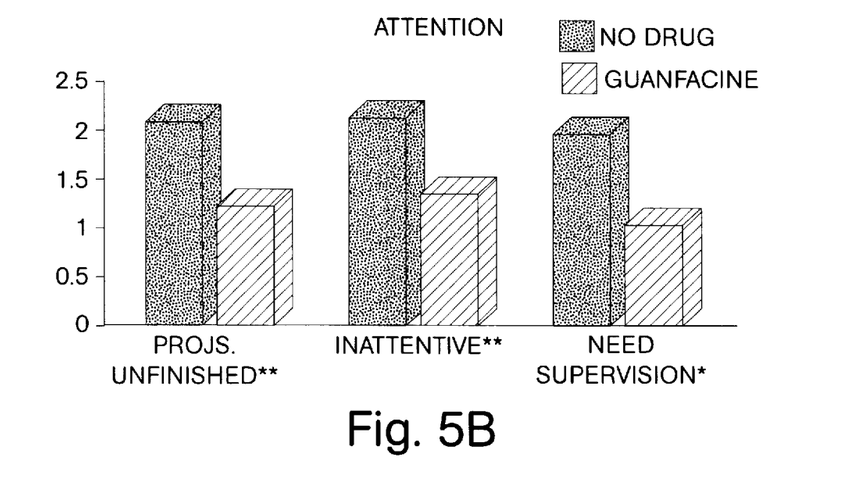
Figure 5C:
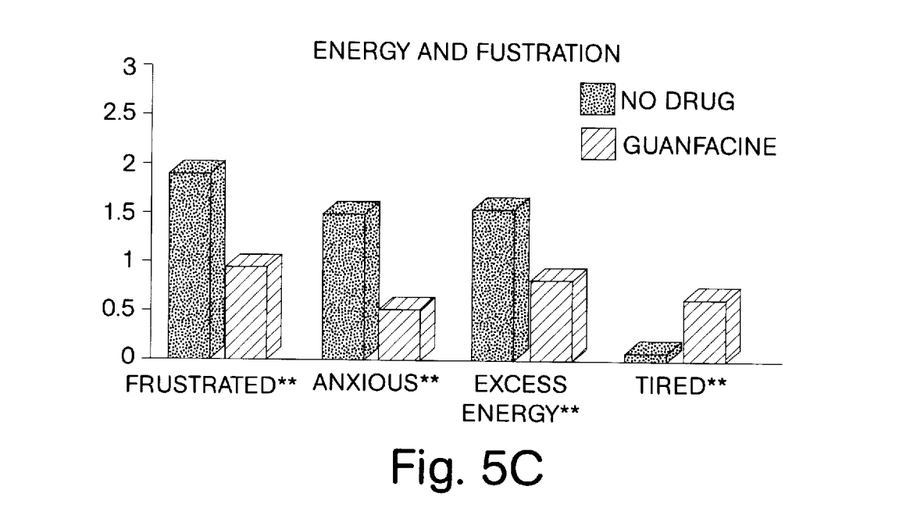

Analysis of the individual items within the Conners' Factors demonstrated specific effects of guanfacine (see FIGS. 5A–C, Table 5). The children were less fidgety (1.85 off, 0.85 on, t=3.61, p<0.002), less restless (1.85 off, 1.08 on, t=2.99, p<0.01) and less likely to make disruptive sounds such as humming and odd noises (1.69 off, 0.85 on, 3.09, p<0.01). In addition, patients were less easily frustrated (2.31 off, 1.17 off, t=3.41, p<0.005), less anxious (1.85 off, 0.69 on, t=3.81, p<0.01) and were more tired during the initial period of treatment (0.14 off, 0.85 on, t=−3.39, p<0.01). However, patients were neither sedated nor impaired in functioning, and did not show significant increases in sleepiness (0.38+/−0.31 off drug, 0.62+/−0.96 on guanfacine (mean +/− S.D.); p>0.4). Interestingly, ten of the subjects (nine male, one female, age range three to eleven years) had previously been treated with clonidine, thus allowing direct comparison between the sedative effects of clonidine and guanfacine. Doses of clonidine (0.2–0.75 mg/day) that produced comparable behavioral calming produced significantly higher sleepiness ratings than found with guanfacine (guanfacine: 0.3+/−1.5; clonidine: 1.0+/−1.1 (mean +/− S.D.), paired t test=2.09, p=0.033 one-tailed). As the sedative effects of alpha-2 agonists became more apparent with increasing age, it is noteworthy that guanfacine was less sedating even though the patients were older than when they were taking clonidine. Patients treated with guanfacine also were better able to finish projects (2.08 off, 1.23 on, t=3.81, p<0.005), more attentive (2.15 off, 1.38 on, t=2.74, p<0.01), and able to function with less supervision (2.00 off, 1.07 on, t=2.35, p<0.025).

Figure 5D:
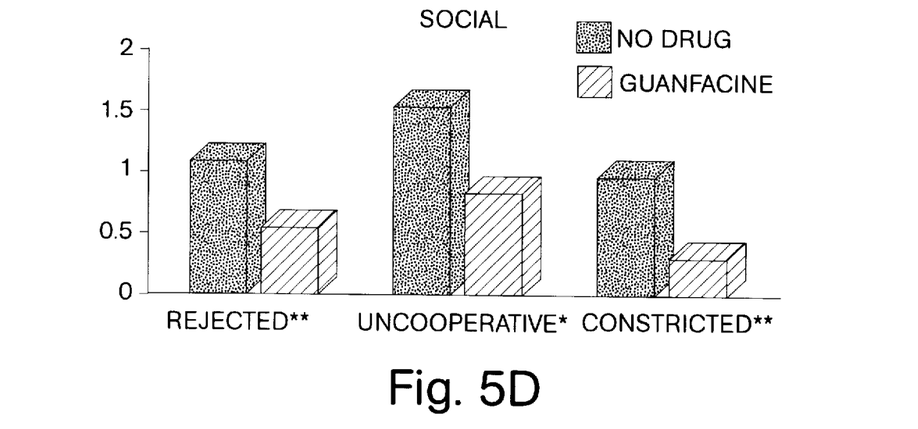

Furthermore, patients improved significantly in some areas of social skills during guanfacine treatment (see FIG. 5D, Table 5). For example, they were less rejected and unpopular in social groups (1.08 off, 0.54 on, t=3.21, p<0.01), less uncooperative (1.54 off, 0.85 on, t=1.81, p<0.05) and less constricted or rigid (1.00 off, 0.33 on, t=2.52, p<0.01).

Subjects did not experience any clinically significant changes in blood pressure nor were any dropped from treatment. A mild transient increase in tiredness usually lasted about 2 weeks. In some cases (16%), a trend toward decreased appetite, which generally stabilized, was noted. Headaches and stomachaches occurred in about 25% of the patients during the first two weeks. These symptoms disappeared in all but one patient who had mild episodes.

The results of this preliminary clinical study indicate that guanfacine is a beneficial and useful treatment for Attention-Deficit/Hyperactivity Disorder. The major beneficial effects of guanfacine are in behaviors reflective of high levels of arousal and activity and in cognitive aspects of inhibition and selective attention. Guanfacine appears to facilitate voluntary selective processes essential to willful cognition and discriminant attention. Patients appear to benefit from guanfacine by exhibiting decreased irritability and enhanced affect regulation.

The predominant behavioral effects of calming and improved frustration tolerance, occurring at the expense of only slight sedation, appear most beneficial in highly aroused, irritable, hyperactive children. In particular, a wide spectrum of Attention-Deficit/Hyperactivity Disorder patients with associated oppositional-defiant behavior may respond preferentially to guanfacine. Compared to clonidine, guanfacine is less sedating and longer acting. Compared to methylphenidate, guanfacine may be more effective on hyperactivity, low frustration tolerance, and high anxiety.

EXAMPLE 5

THE EFFECT OF ADMINISTERING GUANFACINE TO CHILDREN AND ADOLESCENTS WITH TOURETTE'S SYNDROME

For treating children and adolescents having prominent symptoms of Tourette's syndrome, administer guanfacine at doses ranging between 0.01 mg/kg of body weight and 0.25 mg/kg of body weight. Guanfacine was tested in six male subjects, ranging in age from five to fifteen years, who met DSM-IV criteria for Tourette's syndrome. Doses ranged from 2.5–5.0 mg/day. Parent ratings were utilized to assess the level of severity using a four point scale, whereby 0 indicates no tics observed; 1 indicates mild tics observed (approximately one or less per hour); 2 indicates moderate tics observed (approximately one every five minutes); and 3 indicates severe tics observed (approximately one or more per minute). Prior to guanfacine treatment, the mean +/− S.D. tic ratings were 1.83+/−0.56. During guanfacine treatment, tic ratings significantly improved to a mean +/− S.D. of 0.66+/−0.66 (two-tailed T dependent test; no drug vs. guanfacine: p=0.013). Thus, guanfacine may be particularly helpful for children and adolescents with tics who cannot take stimulant medications.

Based on these successful results in monkeys and patients, the Yale Child Study Center (including Dr. Arnsten) initiated an open trial of guanfacine in patients with comorbid Attention-Deficit Hyperactivity Disorder and Tourette's syndrome. Guanfacine significantly improved attention regulation as indicated by improved parent ratings on the Connors scale, and improved performance of a Continuous Performance task. It also produced a mild beneficial effect on tic ratings (Chapell, P. B. et al., (in press) Guanfacine Treatment of Comorbid Attention Deficit Hyperactivity Disorder and Tourette's Syndrome: Preliminary Clinical Experience, J. Amer. Acad. Child and Adolesc. Psychiat.)

SUMMARY OF THE RESULTS

TABLE 1

THE EFFECTS OF INCREASING DOSE OF GUANFACINE ON BEHAVIOR IN A YOUNG RHESUS MONKEY

| Monkey | Dose (mg/kg) | Average No. Trials (correct/ completed) | Median Agitation/ Sedation rating score | Observations |
|---|---|---|---|---|
| #636 | 0 | 10.51/15.3 | −IV | too agitated to complete testing |
|  | 0.001 | 11/17 | −IV | too agitated to complete testing |
|  | 0.011 | 21/30 | −II | slight agitation |
|  | 0.053 | 16/23 | 0 | normal |
|  | 0.11 | 22/28 | −II, then I | began a bit agitated, but then sat quietly |
|  | 0.53 | 19/30 | −II | slight agitation |

TABLE 2

THE EFFECTS OF 0.53 mg/kg GUANFACINE ON BEHAVIOR IN A YOUNG RHESUS MONKEY: EXAMPLES OF REPLICATIONS

| Monkey | Dose (mg/kg) | Average No. Trials (correct/ completed) | Median Agitation/ Sedation rating score | Observations |
|---|---|---|---|---|
| #643 | 0 | 0/0 | −IV | too agitated to test |
|  | 0.53 | 23/30 | −II to I | vocal and circling, then calmer |
|  | 0 | 16/25 | −IV | too agitated to complete testing |
|  | 0.53 | 30/30 | −II | fast, active |
|  | 0 | 20/30 | −III | agitation interfered with performance |
|  | 0.53 | 27/30 | 0 | normal behavior, attentive |
|  | 0 | 0/0 | −IV | too agitated to test |
|  | 0.53 | 30/30 | −I | alert and vocal |

TABLE 3

THE EFFECTS OF GUANFACINE ON BEHAVIOR IN AGED RHESUS MONKEYS

| Monkey | Dose (mg/kg) | Average No. Trials (correct/ completed) | Agitation/ Sedation rating score | Observations |
|---|---|---|---|---|
| #124 | 0 | 18/30 | −II | repeated turning to back of cage, inattentive at times |
|  | 0.11 | 19/30 | −II | same as above |
|  | 0 | 20/30 | −II | same as above |
|  | 0.2 | 26/30 | −I and I | calm but alert, not turning to back of cage |

TABLE 3-continued

THE EFFECTS OF GUANFACINE ON BEHAVIOR IN
AGED RHESUS MONKEYS

| Monkey | Dose (mg/kg) | Average No. Trials (correct/completed) | Agitation/Sedation rating score | Observations |
|---|---|---|---|---|
| #447 | 0 | 18/30 | -II | nervous, easily frustrated, distracted, aggressive when wrong |
|  | 0.011 | 18/30 | -II | same, but less aggressive |
|  | 0 | 17/30 | -II | nervous, easily frustrated, distracted, aggressive when wrong |
|  | 0.11 | 21/30 | I | calmer and more focused |
| #446 | 0 | 21/30 | 0 | normal, but very aggressive |
|  | 0.11 | 20/30 | 0 | same as above |
|  | 0 | 22/30 | 0 | same as above |
|  | 0.15 | 21/30 | 0 | less aggressive than normal |
| #448 | 0 | 20/30 | 0 | normal, but very aggressive; 3 threat contests in 17 min. |
|  | 0.53 | 28/30 | I | calm and much less aggressive; no threat contests |

TABLE 4

THE EFFECTS OF CLONIDINE ON BEHAVIOR IN
AGED RHESUS MONKEYS

| Monkey | Dose (mg/kg) | Average No. Trials (correct/completed) | Observations* |
|---|---|---|---|
| #124 | 0 | 20/30 | Aggressive |
|  | 0.04 | 27/30 | Very quiet, slow moving. Almost seemed sleepy |
|  | 0 | 21/30 | "She was her crazy self" |
|  | 0.05 | 23/30 | Very quiet. She did all things slowly . . . seemed sleepy and uncoordinated |
| #447 | 0 | 20/30 | Distracted, lying down and getting up |
|  | 0.03 | 20/30 | Sedated a bit-in waves, often inattentive |
|  | 0 | 21/30 | Usual self |
|  | 0.06 | 28/30 | Falling asleep intermittently |
| #446 | 0 | 21/30 | Aggressive |
|  | 0.04 | 23/30 | Sleepy but performing task |
|  | 0 | 20/30 | Aggressive |
|  | 0.07 | 21/30 | Sleepy but performing task slowly |
| #448 | 0 | 16/30 | Aggressive; throwing plaques |
|  | 0.05 | 25/30 | occasional eyes closed, sometimes alert |

TABLE 4-continued

THE EFFECTS OF CLONIDINE ON BEHAVIOR IN
AGED RHESUS MONKEYS

| Monkey | Dose (mg/kg) | Average No. Trials (correct/completed) | Observations* |
|---|---|---|---|

*clonidine experiments were conducted in aged monkeys prior to the development of the agitation/sedation rating scale in the other experiments

TABLE 5

SELECTED ITEMS ORDERED BY LEVEL OF SIGNIFICANT
CHANGE FROM BASELINE TO GUANFACINE

| Less Anxious | $P < 0.001$ |
|---|---|
| Less Excess Energy | $P < 0.001$ |
| Better at Finishing Projects | $P < 0.001$ |
| Less Fidgety | $P < 0.002$ |
| Less Easily Frustrated | $P < 0.003$ |
| More Tired | $P < 0.003$ |
| Less Rejected/Unpopular | $P < 0.004$ |
| Less Disruptive Noises | $P < 0.005$ |
| Less Restless | $P < 0.006$ |
| Less Inattentive | $P < 0.009$ |
| Less Constricted/Rigid | $P < 0.010$ |
| Less Need for Supervision | $P < 0.025$ |
| Less Uncooperative | $P < 0.050$ |

What is claimed is:

1. A method of treating a behavioral disinhibition in a primate without inducing excessive sedation, comprising
administering to the primate a behavior inhibiting dose of guanfacine, wherein the dose ranges between 0.01 mg/kg of body weight and 0.86 mg/kg of body weight.

2. The method of claim 1, comprising the additional step of readministering the dose at an interval required to obtain a desired level and duration of behavioral inhibition.

3. The method of claim 1, wherein the primate is a rhesus monkey.

4. The method of claim 1, wherein the primate is a human.

5. The method of claim 4, wherein the dose ranges between about 0.03 mg/kg of body weight and about 0.25 mg/kg of body weight.

6. The method of claim 1, wherein the behavioral disinhibition is one of Attention-Deficit Hyperactivity Disorder, Conduct Disorder, Oppositional-Defiant Disorder, Tourette's Syndrome, Lesch-Nyhan Syndrome, Post-Traumatic Stress Disorder and dementia.

7. A method of inhibiting a disinhibitory behavior in a primate without inducing excessive sedation, comprising:
administering to the primate a behavior inhibiting dose of guanfacine, wherein the dose ranges between 0.01 mg/kg of body weight and 0.86 mg/kg of body weight.

8. The method of claim 7, comprising the additional step of readministering the dose at an interval required to obtain a desired level and duration of behavioral inhibition.

9. The method of claim 7, wherein the primate is a rhesus monkey.

10. The method of claim 7, wherein the primate is a human.

11. The method of claim 10, wherein the dose ranges between about 0.03 mg/kg of body weight and about 0.25 mg/kg of body weight.

12. The method of claim 7, wherein the behavior is one of hyperactivity, agitation, impulsivity, aggression, inattention, distractibility, disorganization, uncontrolled movements, and self-mutilation.

* * * * *

Disclaimer and Dedication

5,854,290 — Amy F. T. Arnsten, Bethany, CT; Patricia S. Goldman-Rakic, New Haven, CT; Robert H. Hunt, Nashville, TN. USE OF GUANFACINE IN THE TREATMENT OF BEHAVIORAL DISORDERS. Patent dated December 29, 1998. Disclaimer filed March 22, 2012 by the Inventors.

Hereby disclaims and dedicates to the public, all claims of said patent.

*(Official Gazette, May 1, 2012)*